(12) United States Patent
Al Zuhair et al.

(10) Patent No.: US 12,275,978 B1
(45) Date of Patent: Apr. 15, 2025

(54) SYSTEM AND METHOD FOR $CO_2$ HYDROGENATION USING MULTI-ENZYME IMMOBILIZATION ON MODIFIED METAL-ORGANIC FRAMEWORK (MOF)

(71) Applicant: United Arab Emirates University, Al Ain (AE)

(72) Inventors: Sulaiman Al Zuhair, Al Ain (AE); Shadeera Rouf, Al Ain (AE); Yaser Mohamed Greish, Al Ain (AE); Bart van der Bruggen, Al Ain (AE)

(73) Assignee: UNITED ARAB EMIRATES UNIVERSITY, Al-Ain (AE)

( * ) Notice: Subject to any disclaimer, the term of this patent is extended or adjusted under 35 U.S.C. 154(b) by 0 days.

(21) Appl. No.: 18/767,461

(22) Filed: Jul. 9, 2024

(51) Int. Cl.
*B01D 53/04* (2006.01)
*C12N 9/02* (2006.01)
*C12N 9/04* (2006.01)
*C12N 9/88* (2006.01)
*C12N 11/14* (2006.01)
*C12N 11/18* (2006.01)
*C12P 7/40* (2006.01)

(52) U.S. Cl.
CPC .............. *C12P 7/40* (2013.01); *C12N 9/0006* (2013.01); *C12N 9/0093* (2013.01); *C12N 9/88* (2013.01); *C12N 11/14* (2013.01); *C12N 11/18* (2013.01); *C12Y 101/01047* (2013.01); *C12Y 117/01* (2013.01); *C12Y 402/01001* (2013.01)

(58) Field of Classification Search
CPC ........ B01D 2253/204; B01D 2257/504; B01D 53/1475; B01J 20/226; B01J 20/3085; B01J 20/3433; C12P 1/04; C12P 7/065

USPC ......................................................... 435/136
See application file for complete search history.

(56) References Cited

U.S. PATENT DOCUMENTS 11,413,565 B2 * 8/2022 Casey et al.
2021/0138385 A1 * 5/2021 Casey et al. ......... B01J 20/3433

* cited by examiner

*Primary Examiner* — Robert B Mondesi
*Assistant Examiner* — Mohammad Y Meah
(74) *Attorney, Agent, or Firm* — MH2 Technology Law Group, LLP

(57) ABSTRACT

There is disclosed a highly stable biocatalytic multi-enzyme system on hydrophobic support for the efficient and continuous hydrogenation of carbon dioxide ($CO_2$) to formate. The system immobilizes formate dehydrogenase (FDH), glucose dehydrogenase (GDH), and carbonic anhydrase (CA) enzymes on a hydrophobic surface-modified metal-organic framework (MOF), SA-HKUST-1. The hydrophobic surface modification with stearic acid enhances the enzyme stability and reusability, maintaining 95% activity after four cycles. The hydrophobicity of SA-HKUST-1 improves $CO_2$ diffusion to the immobilized enzymes, significantly boosting the formate production. Enzyme specificity ensures selective reactions, with FDH facilitating $CO_2$ bioconversion, CA accelerating $CO_2$ hydration and GDH facilitating cofactor regeneration within the system. The system demonstrates superior performance, producing 255.8 mM formate per gram of MOF per hour. Operating under mild conditions with simple equipment, it reduces costs and eliminates harmful by-products. This invention offers an eco-friendly, sustainable approach for $CO_2$ mitigation, with potential applications in industrial $CO_2$ conversion processes.

19 Claims, 13 Drawing Sheets

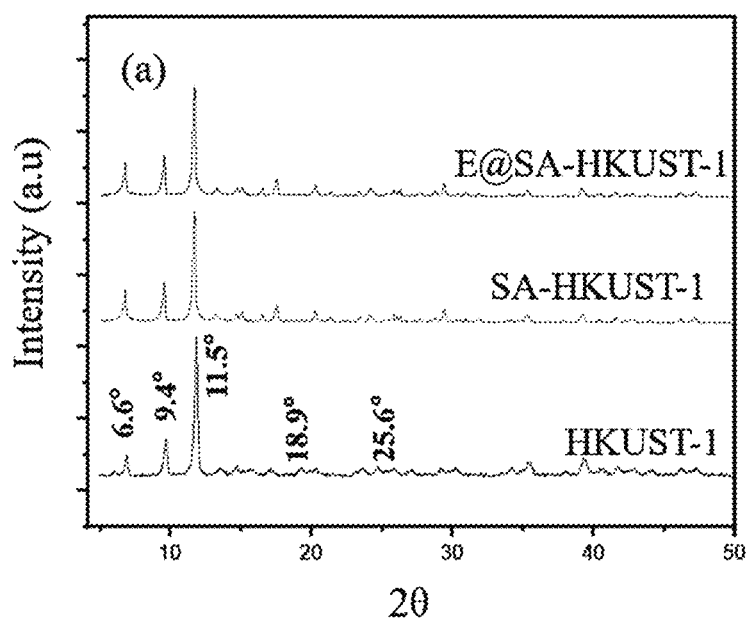
FIG. 1A - XRD patterns of HKUST-1, SA-HKUST-1 and E@SA-HKUST-1
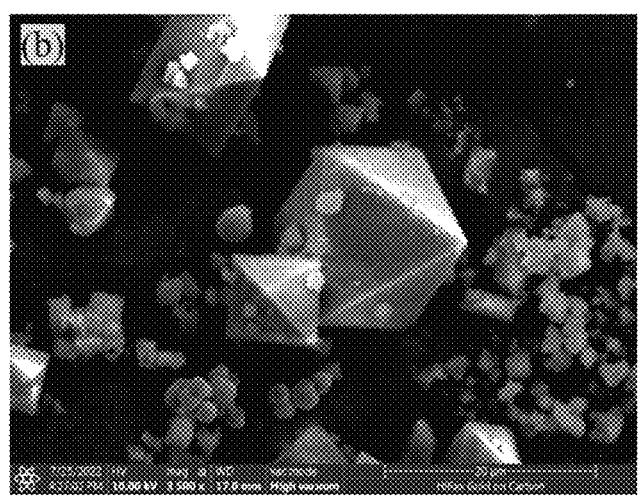
FIG. 1B - SEM image of SA-HKUST-1

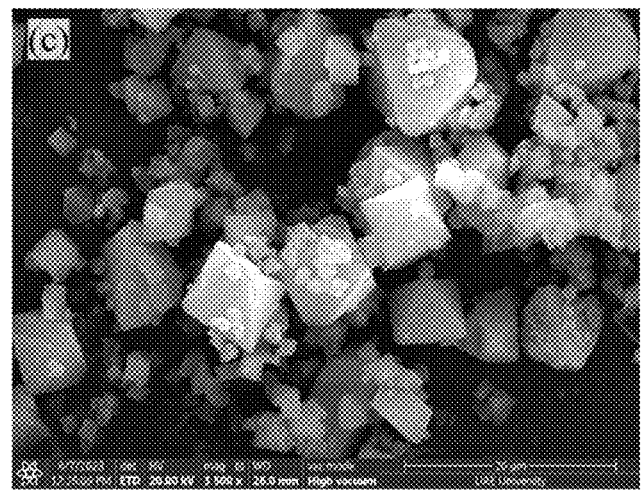
FIG. 1C - SEM image of E@SA-HKUST-1
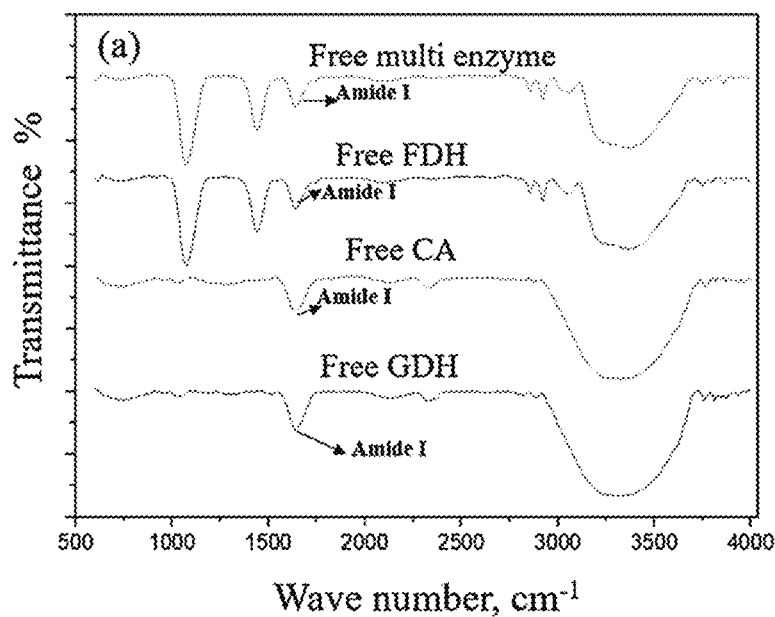
FIG. 2A - FT-IR spectrum of free enzymes

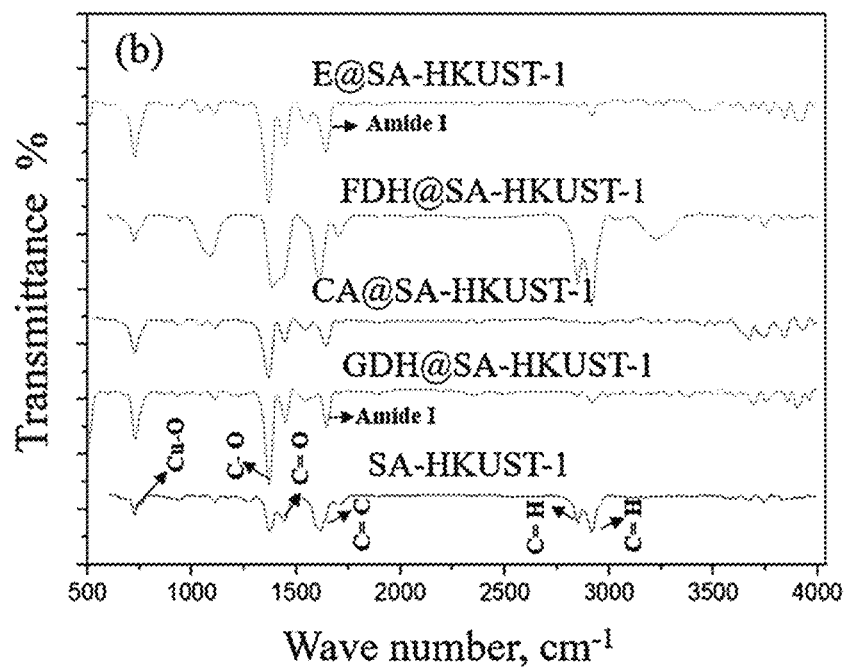
FIG. 2B - FT-IR spectrum of SA-HKUST-1, before and after enzyme immobilization
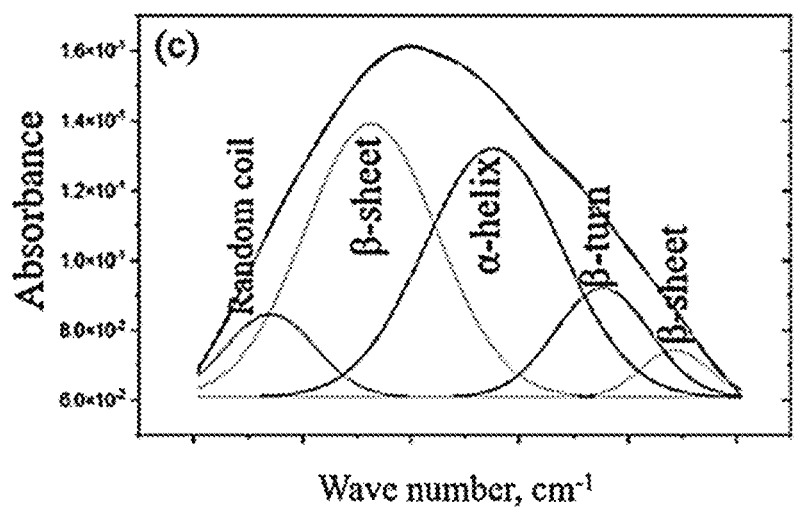
FIG. 2C - Deconvoluted FT-IR peaks (1600 cm$^{-1}$ to 1700 cm$^{-1}$) of free GDH

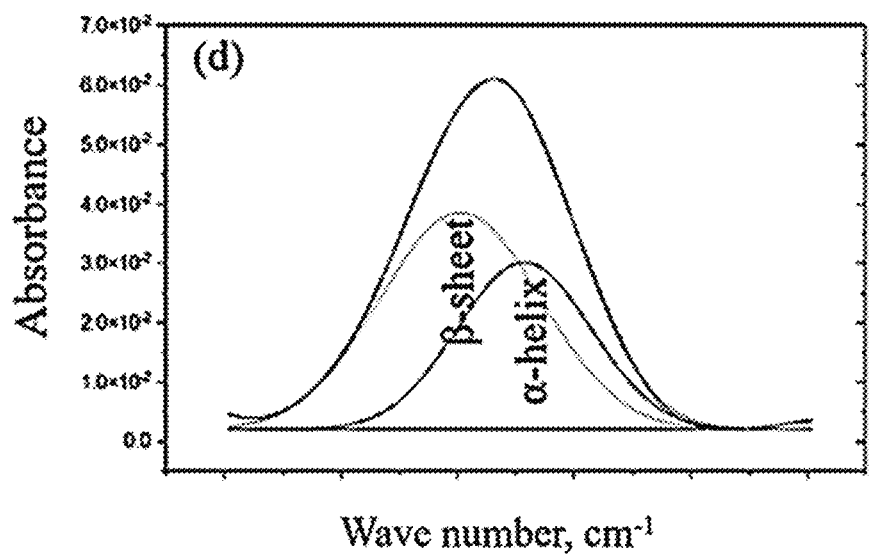
FIG. 2D - Deconvoluted FT-IR peaks (1600 cm$^{-1}$ to 1700 cm$^{-1}$) of GDH@SA-HKUST-1
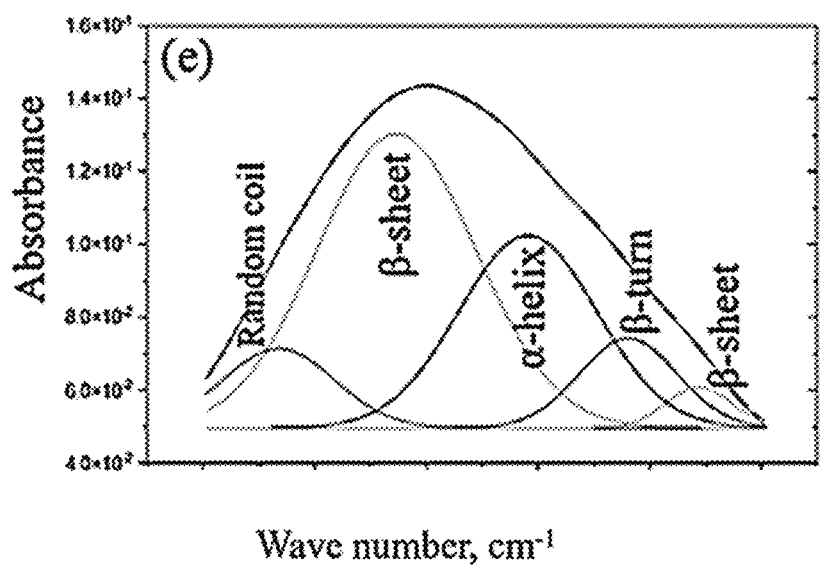
FIG. 2E - Deconvoluted FT-IR peaks (1600 cm$^{-1}$ to 1700 cm$^{-1}$) of free CA

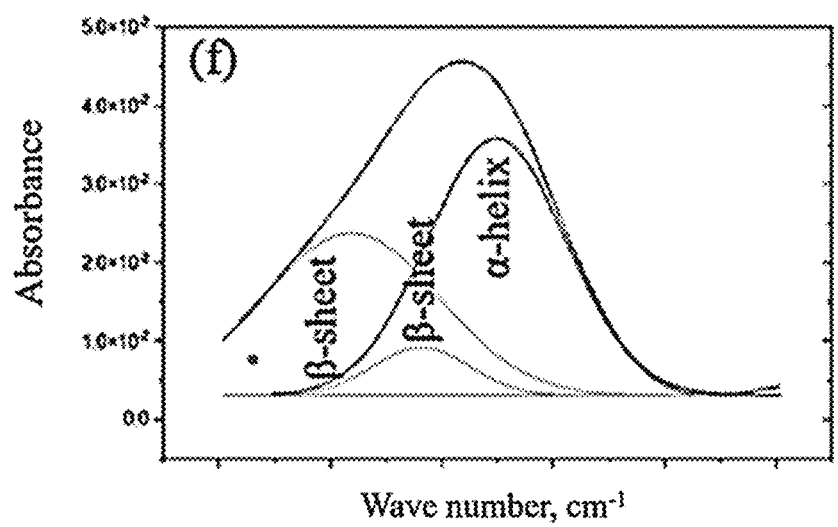
FIG. 2F - Deconvoluted FT-IR peaks (1600 cm$^{-1}$ to 1700 cm$^{-1}$) of CA@SA-HKUST-1
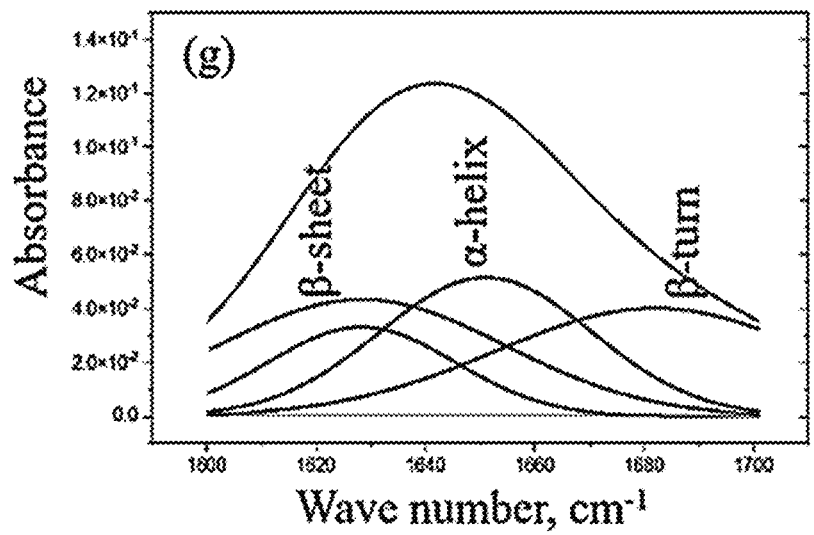
FIG. 2G - Deconvoluted FT-IR peaks (1600 cm$^{-1}$ to 1700 cm$^{-1}$) of free FDH

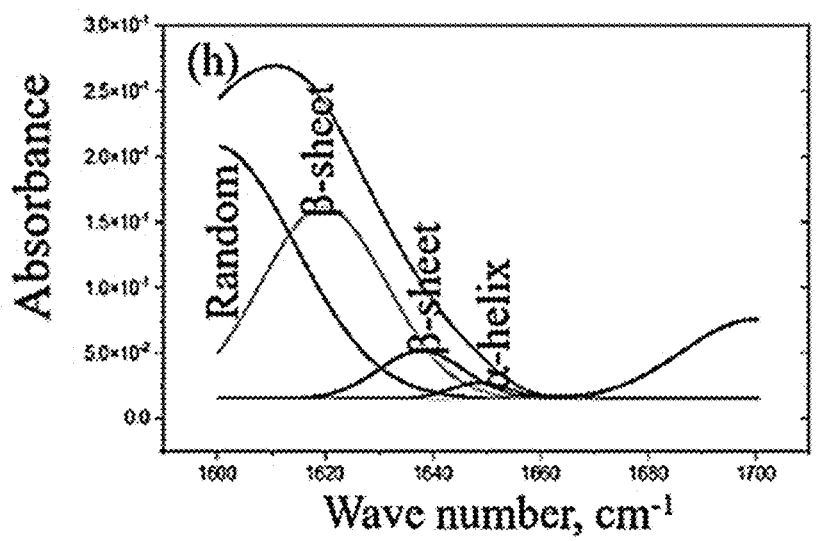
FIG. 2H - Deconvoluted FT-IR peaks (1600 cm$^{-1}$ to 1700 cm$^{-1}$) of FDH@SA-HKUST-1
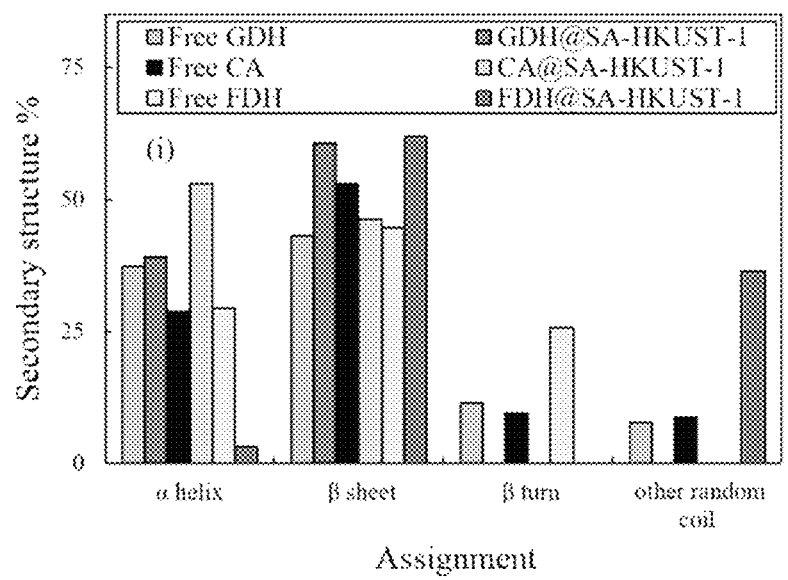
FIG. 2I - Secondary structure assignment for free and immobilized CA, GDH and FDH

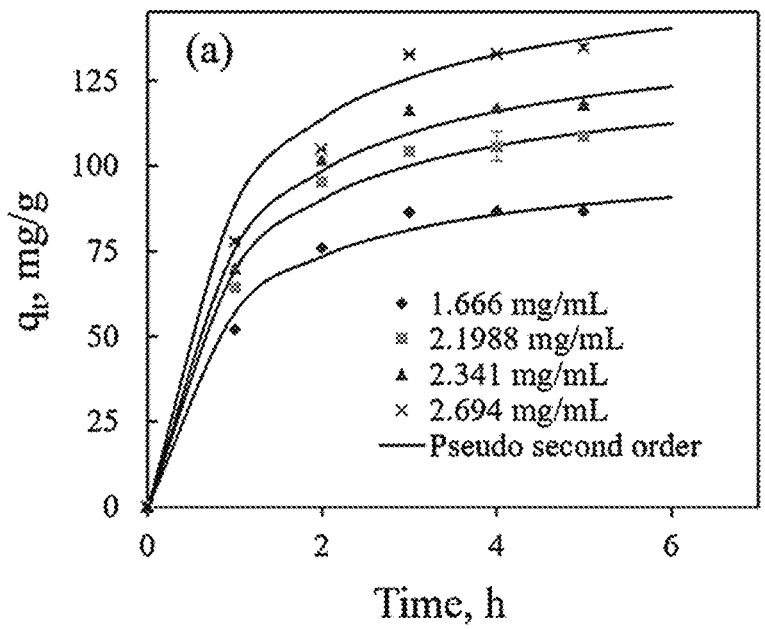
FIG. 3A - Adsorption kinetics of multi enzyme on SA-HKUST-1
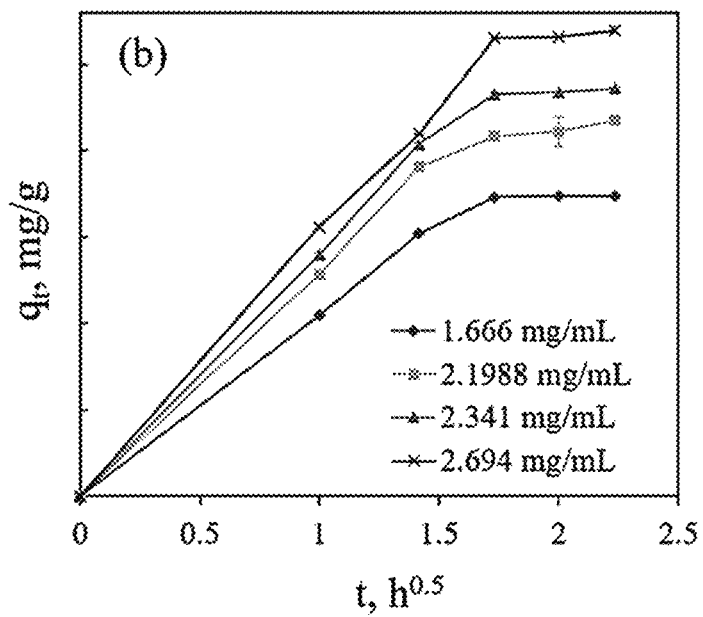
FIG. 3B - Intraparticle diffusion model of multi enzyme adsorption on SA-HKUST-1 at different enzyme loadings

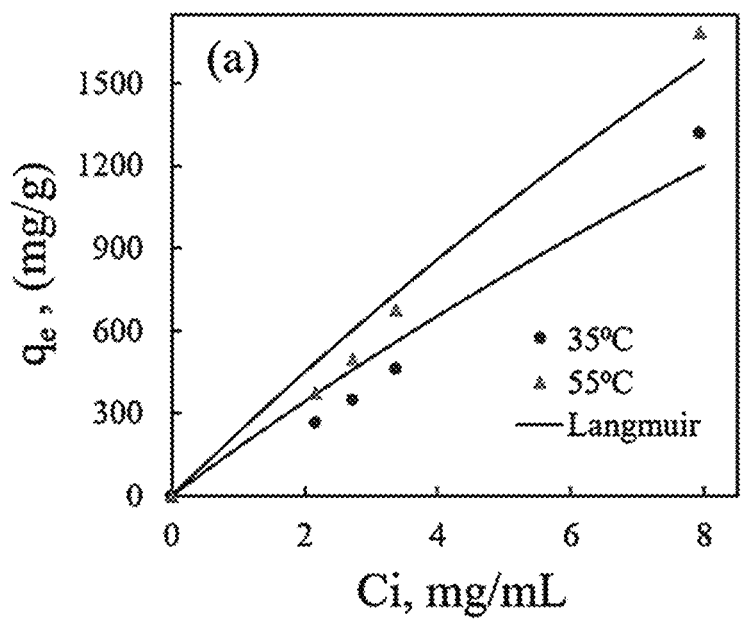
FIG. 4A – Langmuir isotherm model fitting of multienzyme adsorption on SA-HKUST-1
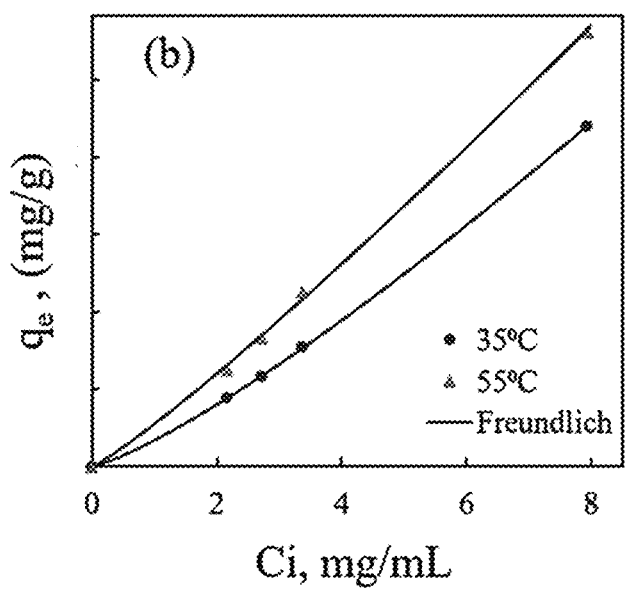
FIG. 4B – Freundlich isotherm model fitting of multienzyme adsorption on SA-HKUST-1

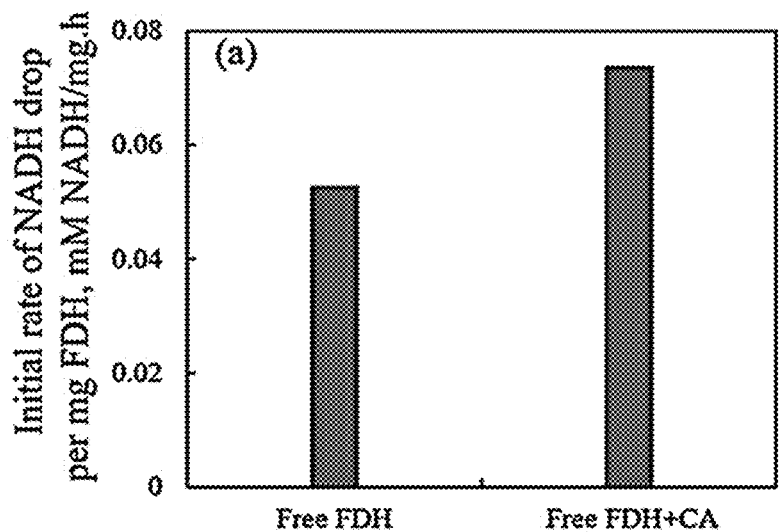
FIG. 5A - Activity of FDH per mg protein with and without CA
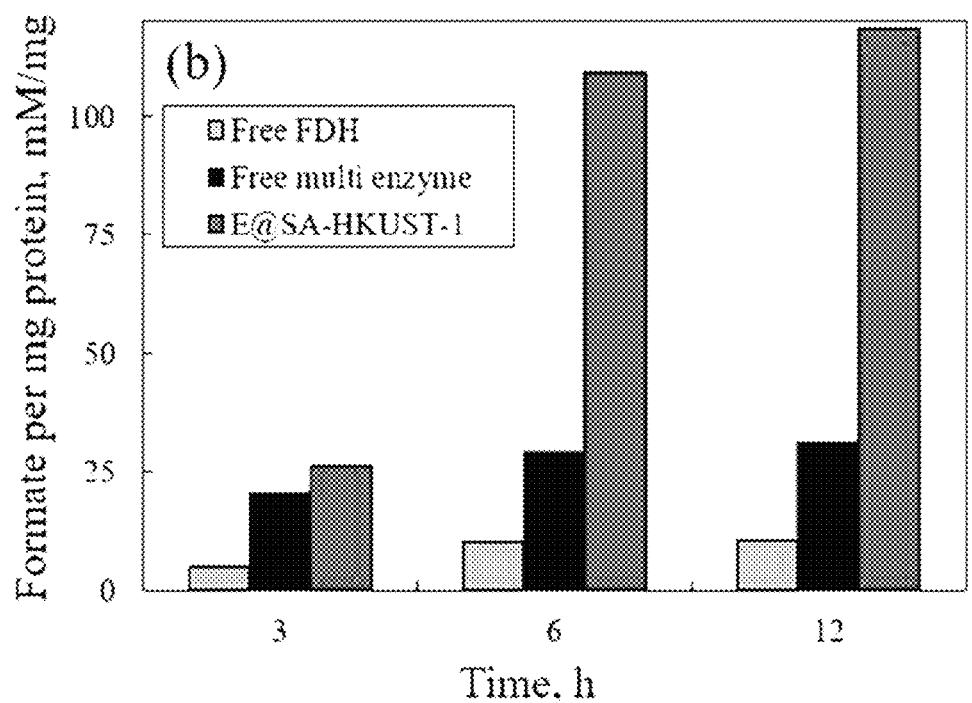
FIG. 5B - Formate production per mg protein by free FDH, free multi-enzymes and E@SA-HKUST-1

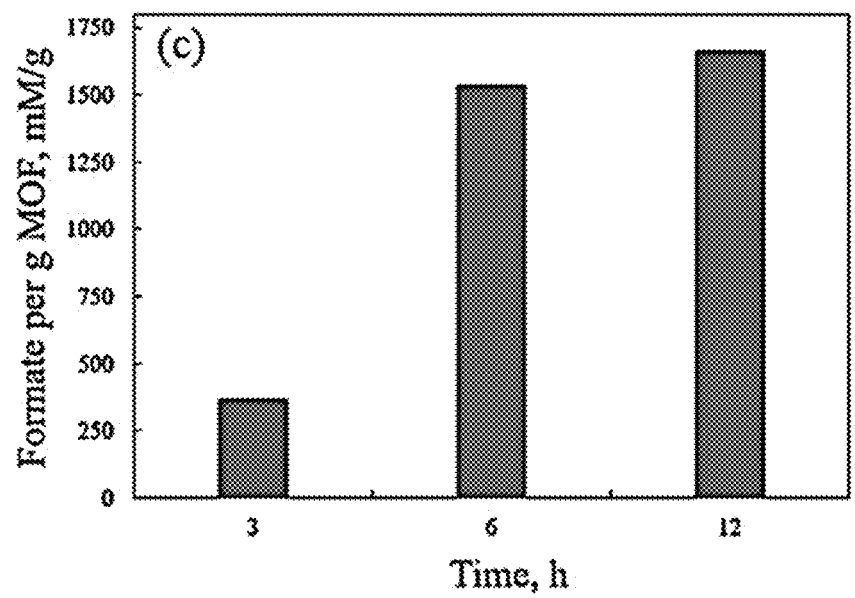
FIG. 5C - Formate production per g MOF using E@SA-HKUST-1
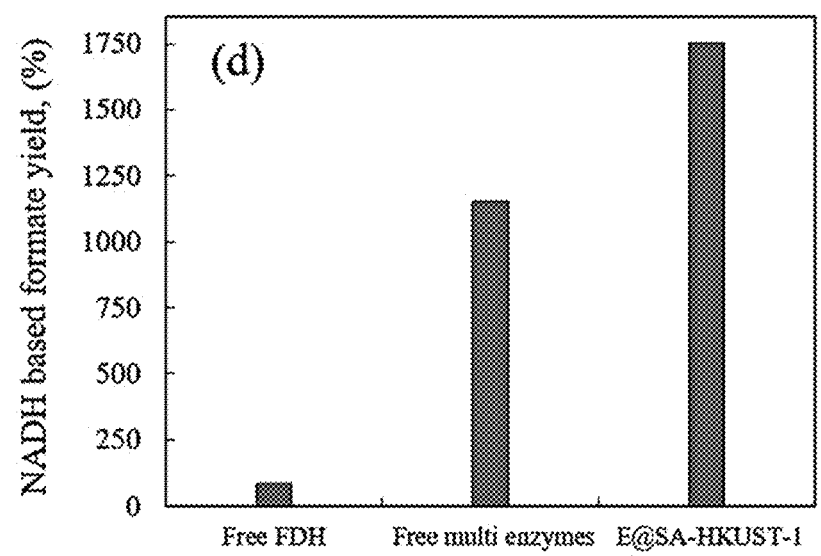
FIG. 5D - NADH based formate yield (%) using free FDH, free multi enzymes and E@SA-HKUST-1

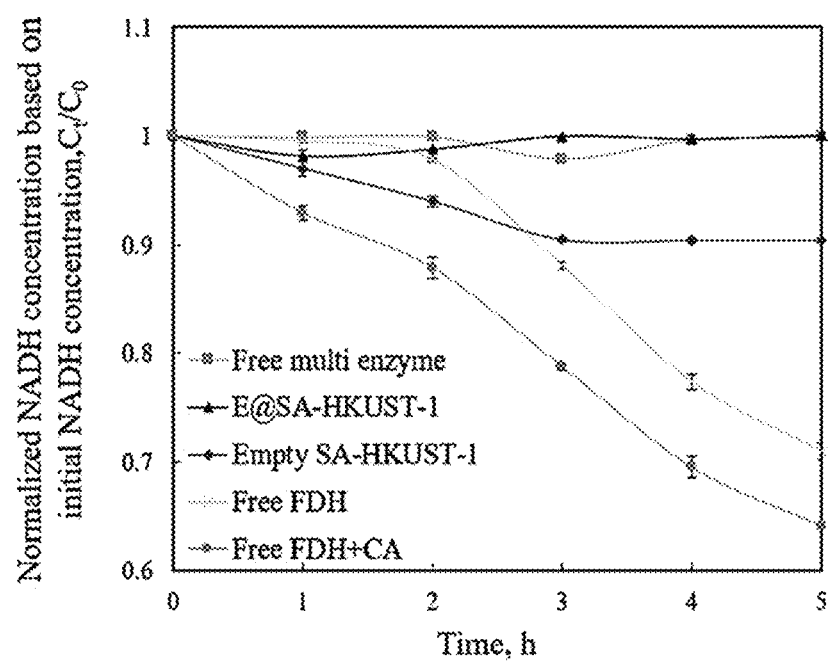
FIG. 6 - Normalized NADH concentration at any time t ($C_t$) with respect to the initial NADH concentration ($C_0$) using free FDH, free FDH + CA, free multi enzymes, empty SA-HKUST-1 and E@SA-HKUST-1

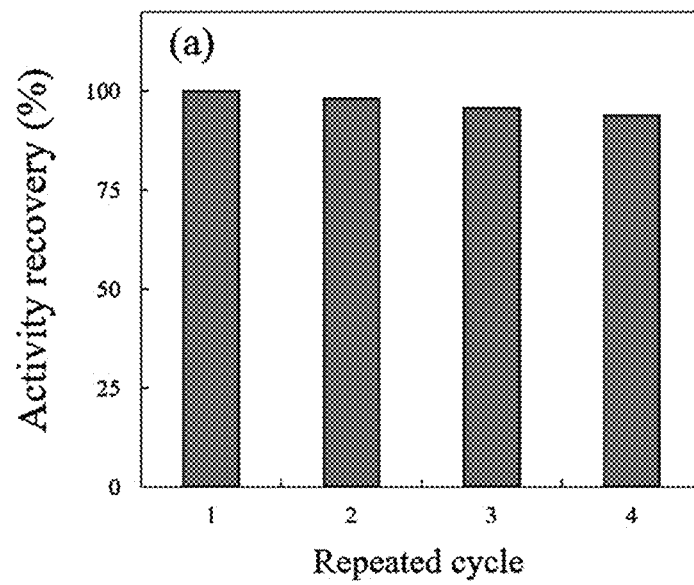
FIG. 7A - Reusability of E@SA-HKUST-1 at pH 7 at 25°C using $CO_2$ as substrate
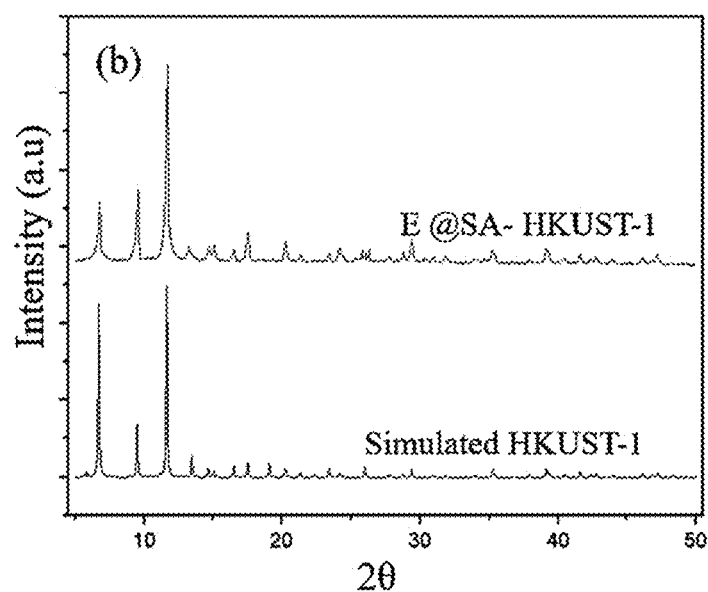
FIG. 7B - XRD pattern of E@SA-HKUST-1 after 4 cycles of repeated use

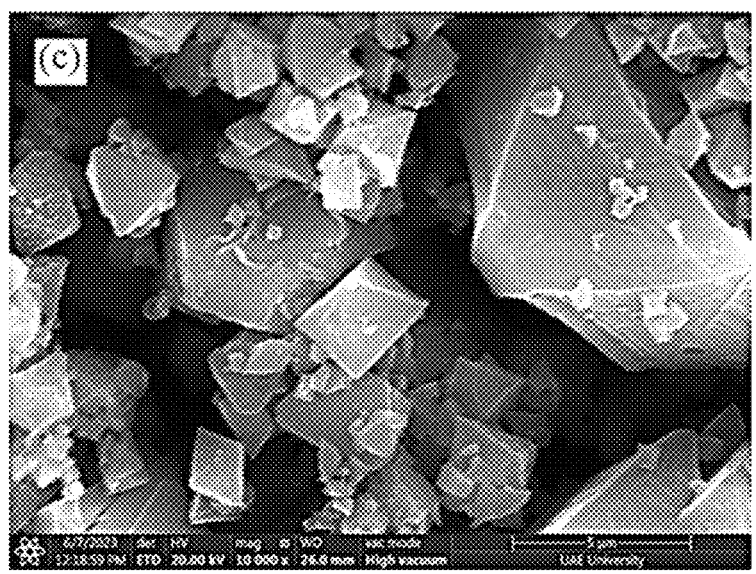
FIG. 7C - SEM image of E@SA-HKUST-1 after 4 cycles of repeated use

SYSTEM AND METHOD FOR $CO_2$ HYDROGENATION USING MULTI-ENZYME IMMOBILIZATION ON MODIFIED METAL-ORGANIC FRAMEWORK (MOF)

FIELD OF THE INVENTION

The present invention relates to the field of enzymatic biocatalysis, and more particularly to methods and systems for enhancing $CO_2$ hydrogenation to formate using multi-enzyme immobilization on modified metal-organic frameworks (MOFs).

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Global warming and climate instability, driven by increased $CO_2$ emissions, have necessitated the development of eco-friendly methods for $CO_2$ mitigation. The bioconversion of $CO_2$ to formate by formate dehydrogenase (FDH) has gained attention as a sustainable solution. FDH facilitates a single-step reversible process, converting $CO_2$ to formate using hydrogen from the cofactor NADH. The produced formate, convertible to formic acid, serves as an excellent hydrogen storage material and finds application in various energy storage means.

Despite its potential, the practical application of FDH encounters significant challenges due to the enzyme's poor stability and limited reusability. The process also necessitates the use of costly NADH in stoichiometric amounts, increasing overall costs. NADH is oxidized as the forward reaction progresses, and its depletion restricts the availability of $H_2$ required for hydrogenation. Additionally, FDH's relatively higher affinity for NAD and formate makes the reverse reaction (formate oxidation) more favorable than $CO_2$ hydrogenation, leading to NAD accumulation within the system. Furthermore, the high thermodynamic stability and low solubility of $CO_2$ result in slow reaction kinetics and low formate production. These challenges limit the $CO_2$ hydrogenation process and significantly reduce the equilibrium conversion. Overcoming these challenges and sustaining a high forward reaction rate require maintaining a high NADH concentration throughout the reaction.

Analysis of related prior art in the field of $CO_2$ hydrogenation showed discussions of NADH regeneration based on chemical, electrochemical, and photochemical methods. Chemical regeneration is cost-effective, utilizing commercially available reagents with high redox potential. However, its application is limited by low compatibility with biological systems, low productivity, potential enzyme deactivation, low cofactor turnover, and difficult product isolation. Electrochemical methods offer good redox potential control and ease of product recovery but suffer from poor biochemical compatibility, low selectivity for reductive regeneration, electrode fouling, and the need for complex equipment and redox reagents. Photochemical systems require expensive, complex apparatuses and are incompatible with biological systems, and necessitates redox dyes and photosensitizers.

Biological regeneration using enzymes is reported but has drawbacks associated with them such as high cost, poor operational stability, reusability issues, and difficult product separation. Out of several enzymes available for NADH regeneration, the enzyme glutamate dehydrogenase (GDH) has been selected because of its high affinity for NAD to compete with FDH in utilizing NAD as substrate instead of NADH. Glutamate dehydrogenase GDH is also less expensive compared to other commercially available NADH regenerating enzymes. Choosing the right support material is crucial for enzyme activity, stability, and reusability of enzymes in the reaction. Prior art discusses using metal-organic frameworks (MOFs) like ZIF-8, HKUST-1 and UiO66-$NH_2$, but enzyme confinement within the support matrices increases diffusion resistance of substrates and products, resulting in low activity. MOFs such as ZIF-8 and HKUST-1 also exhibit poor stability in acidic $CO_2$ environments and moisture, limiting practical application at an industrial level.

Based on the above explained, there exists a need for a better support material and system for $CO_2$ hydrogenation to formate by FDH, which overcomes the drawbacks of the traditionally employed systems.

SUMMARY OF THE INVENTION

Therefore it is an object of the present invention to propose a biocatalytic multienzyme system consisting of a selected combination of enzymes immobilized on hydrophobic modified metal-organic framework (MOF) for enhanced carbon dioxide ($CO_2$) hydrogenation to formate.

There is disclosed a biocatalytic multienzyme system for the enhanced hydrogenation of carbon dioxide ($CO_2$) to formate, comprising: a hydrophobic modified metal-organic framework (MOF) SA-HKUST-1 as support material, produced by surface-modification of HKUST-1 MOF with stearic acid; and a combination of plurality of enzymes including formate dehydrogenase (FDH), carbonic anhydrase (CA), and glutamate dehydrogenase (GDH) immobilized on a hydrophobic surface of the SA-HKUST-1, wherein the hydrophobic surface of the SA-HKUST-1 enhances stability and reusability of the immobilized enzymes, with each enzyme performing a specific role in the overall reaction. The hydrogen source is nicotinamide adenine dinucleotide+hydrogen (NADH) serving as a cofactor.

In an embodiment of the present invention, the HKUST-1 MOF undergoes post-synthetic functionalization by treatment with stearic acid in ethanol to produce modified MOF, SA-HKUST-1, which is hydrophobic in nature.

In an embodiment of the present invention, the biocatalytic multienzyme system immobilizes the plurality of enzymes on the hydrophobic surface of the SA-HKUST-1 instead of encapsulating them within its matrix. This, in turn reduces the mass transfer limitations and enhances formate production.

In another embodiment of the present invention, the hydrophobicity of the SA-HKUST-1 improves the diffusion of $CO_2$ towards the immobilized enzymes attached on its surface, and this leads to an enhanced formate production.

In an embodiment of the present invention, the FDH converts $CO_2$ to formate using hydrogen donated by nicotinamide adenine dinucleotide+hydrogen (NADH) serving as a cofactor in the reaction.

According to the present disclosure, the system produces 255.83 mM formate per gram of MOF per hour (mM/gsupport·h).

In an embodiment of the present invention, the GDH regenerates the cofactor NADH within the system, thereby ensuring a sustained source of hydrogen required for $CO_2$ hydrogenation by the FDH.

In another embodiment of the present invention, the CA accelerates hydration of $CO_2$ and facilitates cost-effective $CO_2$ capture for enabling hydrogenation by the FDH.

In an embodiment of the present invention, the SA-HKUST-1 is stable and reusable in both acidic and aqueous environments, owing to its hydrophobic properties.

In an embodiment of the present invention, the immobilized enzymes on the SA-HKUST-1 are stable and retain at least 95% enzyme activity after four reuse cycles.

In another embodiment of the present invention, the enzymatic system operates under mild conditions and does not produce any harmful byproducts.

In another embodiment of the present invention, the mild operating conditions comprise a pH of 7 and room temperature for the system.

In an embodiment of the present invention, the formate produced has a high hydrogen storage capacity and is used in hydrogen fuel cells and formic acid-powered vehicles.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

FIG. 1A shows XRD patterns of HKUST-1, SA-HKUST-1 and E@SA-HKUST-1 (multi enzymes immobilized on SA-HKUST-1), in accordance with the present invention.

FIG. 1B and FIG. 1C show SEM images of SA-HKUST-1 before and enzyme immobilization respectively, in accordance with the present invention.

FIG. 2A and FIG. 2B show FT-IR spectrum of free enzymes and SA-HKUST-1, before and after enzyme immobilization, respectively, in accordance with the present invention.

FIG. 2C-2H shows deconvoluted FT-IR peaks (1600 $cm^{-1}$ to 1700 $cm^{-1}$) of Free GDH, GDH@SA-HKUST-1, Free CA, CA@SA-HKUST-1, free FDH and FDH@SA-HKUST-1, respectively, in accordance with the present invention.

FIG. 2I shows secondary structure assignment for free and immobilized CA, GDH and FDH, in accordance with the present invention.

FIG. 3A shows the adsorption kinetics of multi enzyme on SA-HKUST-1, in accordance with the present invention.

FIG. 3B shows the intraparticle diffusion model of multi enzyme adsorption on SA-HKUST-1 at different enzyme loadings, in accordance with the present invention.

FIG. 4A and FIG. 4B shows Langmuir and Freundlich isotherm model fitting of multi enzyme adsorption on SA-HKUST-1, respectively, in accordance with the present invention.

FIG. 5A shows the activity of FDH per mg protein with and without CA, in accordance with the present invention.

FIG. 5B shows formate production per mg protein by free FDH, free multi-enzymes and E@SA-HKUST-1 (multi enzymes immobilized on SA-HKUST-1), in accordance with the present invention.

FIG. 5C shows formate production per g MOF using E@SA-HKUST-1 (multi enzymes immobilized on SA-HKUST-1), in accordance with the present invention.

FIG. 5D shows NADH based formate yield (%) using free FDH, free multi enzymes and E@SA-HKUST-1 (multi enzymes immobilized on SA-HKUST-1), in accordance with the present invention.

FIG. 6 shows normalized NADH concentration at any time t ($C_t$) with respect to the initial NADH concentration ($C_0$) using free FDH, free FDH+CA, free multi enzymes, empty SA-HKUST-1 and E@SA-HKUST-1 (multi enzymes immobilized on SA-HKUST-1), in accordance with the present invention.

FIG. 7A shows the reusability of E@SA-HKUST-1 at pH 7 at 25° C. using $CO_2$ as substrate, in accordance with the present invention.

FIG. 7B shows XRD image of E@SA-HKUST-1 (multi enzymes immobilized on SA-HKUST-1) after 4 cycles of repeated use, in accordance with the present invention.

FIG. 7C shows SEM image of E@SA-HKUST-1 (multi enzymes immobilized on SA-HKUST-1) after 4 cycles of repeated use, in accordance with the present invention.

DETAILED DESCRIPTION OF THE INVENTION

The aspects of the proposed biocatalytic multienzyme system for enhanced $CO_2$ hydrogenation to formate-according to the present invention will be described in conjunction with FIGS. 1-7. In the Detailed Description, reference is made to the accompanying figures, which form a part hereof, and which is shown by way of illustration specific embodiments by which the invention may be practiced. It is to be understood that other embodiments may be utilized and logical changes may be made without departing from the scope of the present invention. The following detailed description, therefore, is not to be taken in a limiting sense, and the scope of the present invention is defined by the appended claims.

The present invention proposes a biocatalytic multienzyme system consisting of a selected combination of (three) enzymes immobilized on hydrophobic modified metal-organic framework (MOF) for enhanced carbon dioxide ($CO_2$) hydrogenation to formate. The multienzyme system is developed with the combination of the actions of selected multiple enzymes consisting of carbonic anhydrase (CA), glutamate dehydrogenase (GDH), and formate dehydrogenase (FDH) immobilized on a surface-modified HKUST-1 (MOF). The surface modification of HKUST-1 involves treating HKUST-1 with stearic acid (SA) to produce functionalized form SA-HKUST-1 and is characterized its hydrophobic nature. The system hydrogenates $CO_2$ to formate using formate dehydrogenase (FDH) coupled with an efficient cofactor (NADH) regeneration in the reaction. The combination of three enzymes (FDH, CA and GDH) and the hydrophobicity of the modified MOF, serving as the support material help to improve the reaction kinetics and formate production by FDH. Employing the proposed multienzyme system for the bioconversion of $CO_2$ to formate is a sustainable approach of $CO_2$ mitigation and does not produce any harmful byproducts. In an embodiment of the present invention, the proposed multienzyme system for $CO_2$ hydrogenation to formate is best adapted operate at mild conditions using simple equipment which is cost-effective compared to conventional chemical-based $CO_2$ utilization process.

The features of the synthesized SA-HKUST-1 are described here. It is stable in the presence of acidic and aqueous environment which is essential for practical implementation of the conversion process. The hydrophobicity of the support also enhances $CO_2$ diffusion towards the enzymes attached over its surface. It presents higher formate production and reusability compared to other support materials. Enzymes operate at mild conditions which reduces overall cost of operation compared to conventional chemical-based $CO_2$ utilization process. The enzyme FDH converts $CO_2$ to formate using hydrogen donated by cofactor. The enzyme CA accelerates $CO_2$ hydration and CA based $CO_2$ capture is 25% cost effective compared to the conventional amine-based $CO_2$ capture process. The enzyme GDH regenerates cofactor NADH, which is highly efficient and biocompatible compared to the conventional electrochemical and chemical cofactor regeneration methods. Immobilization of enzymes over hydrophobic support enhances the stability and activity of immobilized enzymes.

The stability and reusability of enzymes can be enhanced by immobilizing the enzymes on suitable support material. The enzymes need to be immobilized on appropriate support material during $CO_2$ hydrogenation reaction to overcome the drawbacks associated with the use of free enzymes, such as high cost, poor operational stability and reusability, and difficult product separation. Selecting the appropriate support material is essential for preserving the activity, stability, and reusability of immobilized enzymes. Metal-organic frameworks (MOFs), are a class of recyclable hybrid materials consisting of metal centers coordinated by organic ligands and are regarded as promising supports for enzyme immobilization due to their high surface area and tunable properties. HKUST-1 is a metal-organic framework (MOF) widely utilized as a support matrix for enzyme immobilization due to its high porosity and large square pores, which endows it with a high retention capacity for enzymes. However, HKUST-1 is hydrophilic and undergoes irreversible decomposition in the presence of moisture or aqueous solutions. To address this instability in aqueous solutions, the proposed disclosure suggests functionalizing the surface with stearic acid (SA). In an embodiment of the present invention, post-synthetic modification of the HKUST-1 is performed using stearic acid in ethanol. This modification transforms HKUST-1 into SA-HKUST-1 (functionalized HKUST-1), enhancing its surface hydrophobicity and stability of HKUST-1 in acidic and aqueous solutions. The hydrophobic surface improves the diffusion of $CO_2$ toward the immobilized enzymes (FDH, GDH, CA) attached over the surface, resulting in increased formate production compared to using free enzymes or enzymes immobilized on other MOFs, such as, ZIF-8, or hydrophilic HKUST-1@MIL-101. FDH on the modified surface produced 13 times more formate than FDH immobilized on the as-prepared hydrophilic HKUST-1@MIL-101.

The SA-HKUST-1 support demonstrates a high retention capacity for the enzymes and exhibits enhanced stability and reusability in aqueous or acidic solutions. High affinity of the hydrophobic support significantly improves $CO_2$ diffusion towards the enzymes, thereby enhancing the stability and reusability of the immobilized enzymes upon repeated use in an aqueous as well as acidic $CO_2$ environments. The enhanced stability of enzymes can be attributed to the prevention of subunit dissociation and unfolding of the protein. The proposed SA-modified HKUST-1 multienzyme system presents a high reusability by retaining 95% enzyme activity after four reuse cycles compared with other MOFs used. ZIF-8 is found to be unstable in the presence of acidic $CO_2$ and formic acid and retains only 65% activity after 4 cycles of repeated use. Hydrophilic HKUST-1 undergoes irreversible decomposition in presence of moisture and, HKUST-1@MIL-101 retains only 57.5% activity after three cycles of reuse. Moreover, the previously used MOF supports encapsulated the enzymes inside the support matrix and this confinement resulted in higher diffusion resistance of the substrate and cofactor (NADH) resulting in low activity and formate production. Unlike these MOF supports used so far, SA-HKUST-1 does not encapsulate the multiple enzymes within its matrix, instead are immobilized by attachment over its modified hydrophobic surface, resulting in low mass transfer resistance for the substrates and products, which in turn leads to high formate production. Using a combination of multiple enzymes and hydrophobic support for surface encapsulation produces 255.8 mM formate per g MOF per h. This is very high compared to the same combination of enzymes encapsulated inside ZIF-8 (30 mM formate per gram MOF per h) and inside HKUST-1@MIL-101 (18.75 mM formate per gram MOF per h).

In an embodiment of the invention, the proposed multienzyme system utilizes the combination of three specific enzymes (FDH, CA and GDH) immobilized on the hydrophobic MOF to improve the reaction kinetics and formate production by FDH. Enzymes are highly specific for reactants and products and can select the desired substrate from a group of molecules. During $CO_2$ hydrogenation reaction, the enzyme formate dehydrogenase (FDH) acts as a biocatalyst and converts $CO_2$ to formate in a single-step reversible process using hydrogen ($H_2$) donated by the cofactor nicotinamide adenine dinucleotide+hydrogen (NADH) according to Equation (1). This bioconversion of $CO_2$ to formate by formate dehydrogenase (FDH) is an ecofriendly approach to reduce $CO_2$ levels.

(1)

As the forward reaction proceeds, NADH is oxidized, and its depletion reduces the availability of $H_2$ needed for hydrogenation. Additionally, due to the relatively higher affinity of FDH for NAD and formate, the reverse reaction (formate oxidation) becomes more favorable than $CO_2$ hydrogenation as NAD accumulates in the system. The process is further slowed and made inefficient by the thermodynamic stability and low solubility of $CO_2$. These challenges are addressed by regenerating the biological cofactor (NADH) through the selection of a second enzyme and co-substrate. In an embodiment of the invention, the dehydrogenase enzyme glutamate dehydrogenase (GDH) is proposed for NADH regeneration due to its high activity, stability, and commercial availability. GDH has a high affinity for NAD, preventing its accumulation within the system and significantly enhancing the equilibrium conversion of $CO_2$. Additionally, GDH remains stable over a wide range of pH and in the presence of organic solvents and catalyses the reversible conversion of glutamate to α-ketoglutaric acid using NAD as a cofactor.

GDH sustains a high forward reaction rate by maintaining a high NADH concentration through continuous regeneration of the cofactor and continuous removal of NAD within the system throughout the reaction. GDH offers several advantages over other dehydrogenases such as formaldehyde dehydrogenase, alcohol dehydrogenase, phosphite dehydrogenase or glucose dehydrogenase for $CO_2$ hydrogenation to formate. It demonstrates high compatibility with biochemical systems, exceptional stability, high selectivity (especially for converting NAD to NADH) and allows easy monitoring of reaction progress. GDH's high affinity for NAD enables it to compete effectively with FDH, utilizing NAD as a substrate instead of NADH. By rapidly utilizing NAD, GDH continuously removes it, preventing its accumulation within the system. Unlike other dehydrogenase (formaldehyde dehydrogenase), GDH prevents the cascade reaction that converts the product, formate, to formaldehyde, ensuring a higher yield of formate. Moreover, GDH regenerates NADH in a highly efficient and biocompatible manner, outperforming conventional electrochemical and chemical cofactor regeneration methods. It is highly compatible with biological systems, exhibits high enzyme activity and selectivity for reductive regeneration, achieves high productivity with a significant cofactor turnover, and facilitates easy product isolation and recovery. GDH does not require costly or complex apparatuses or additional redox reagents for the process. Furthermore, GDH is inexpensive and available for large-scale commercial utilization. Thus, immobilizing a combination of FDH and GDH enzymes on SA-modified HKUST-1 facilitates enhanced $CO_2$ hydrogenation to formate with continuous cofactor regeneration and reaction kinetics. The improved diffusion of $CO_2$ toward FDH on the hydrophobic support surface effectively improves the reaction kinetics and formate production by FDH.

The present disclosure aims to improve the performance of FDH for $CO_2$ hydrogenation to formate by incorporating two specific additional enzymes, GDH and carbonic anhydrase (CA). In an embodiment of the invention, the enzyme carbonic anhydrase (CA) is used to accelerate the enzymatic hydrogenation of $CO_2$. This enzyme catalyzes the hydration of $CO_2$, thereby improving its solubility. The dissolution of $CO_2$ in the presence of CA accelerates formate formation and facilitates a rapid rate of hydrogenation reaction kinetics. In short, adding CA to the reaction system increases the rate of $CO_2$ hydration, which in turn boosts rate of formate production. Thus, in an embodiment, a combination of the enzymes CA, GDH and FDH is tested in a biocatalytic system for $CO_2$ hydrogenation by FDH. GDH successfully regenerates NADH and ensures continuous supply of cofactor required for the reaction thereby enhancing formate yield. Meanwhile, CA accelerates $CO_2$ hydration and facilitates cost-effective $CO_2$ capture compared to conventional $CO_2$ capture processes.

The proposed biocatalytic system for $CO_2$ hydrogenation reaction describes the adsorption kinetics of the multiple enzymes on the SA-HKUST-1 surface using a pseudo-second-order model, while equilibrium follows the Freundlich isotherm. Formate production by the enzymes immobilized on SA-HKUST-1 is found to be 3.75 times higher than that achieved by free enzymes and 8.4 times higher than that of FDH immobilized alone on SA-HKUST-1. The hydrophobic interaction between the enzymes and the support alters the secondary structure of the enzymes, allowing the immobilized enzymes to retain 94% of their activity after four reuse cycles. The disclosure provides insights into the combined effect of hydrophobic support and multiple enzymes on the catalytic efficiency and stability of FDH. These findings provide a basis for developing a highly stable biocatalytic system with cofactor regeneration for the continuous hydrogenation of $CO_2$ to formate at the industrial level.

The multienzyme system discussed herein offers numerous advantages. First of all, the invention offers dual advantage of reducing $CO_2$ emission by forming valuable product, formate using a combination of enzymes (formate dehydrogenase (FDH), carbonic anhydrase (CA) and glutamate dehydrogenase (GDH). These enzymes on surface-modified HKUST-1 can operate at mild conditions such as at pH7 and at room temperature. The multienzyme system is environmentally friendly and does not evolve any harmful products when utilized in $CO_2$ hydrogenation reaction. Immobilization of enzymes over hydrophobic MOF, SA-HKUST-1 enhances the stability and reusability of enzymes desired at industrial level. Also, the process is cost effective compared to conventional $CO_2$ capture processes. The resultant formate produced in very high yields, has high $H_2$ storage capacity and can be used in $H_2$ fuel cells and power formic acid vehicles.

Hydrogenating carbon dioxide to formate by FDH using the proposed multienzyme system is a sustainable approach for $CO_2$ mitigation. The bioconversion of $CO_2$ to formate by the biocatalyst is an eco-friendly method to reduce $CO_2$ levels, thereby combating global warming and climate instability caused by increased $CO_2$ emissions. The result of the present invention clearly underscores the immense potential for the commercial application of this enzyme system in the post-combustion treatment of $CO_2$ and presents a highly stable biocatalytic system with cofactor regeneration for the continuous hydrogenation of $CO_2$ to formate at the industrial level. The reaction yields a high amount of formate, which can be converted into formic acid, an excellent hydrogen storage material and can be used in $H_2$ batteries, power packs or fuel cells, and HCOOH vehicles.

In an embodiment of the present invention, HKUST-1 undergoes post-synthetic modification via surface functionalization with stearic acid (SA) to produce modified HKUST-1, known as SA-HKUST-1. The synthesis of hydrophobic SA-modified HKUST-1 MOF is carried out using trimesic acid ($H_3BTC$) also known as benzene tricarboxylic acid), copper nitrate $Cu(NO_3)_2 \cdot 3H_2O$, dimethyl formamide (DMF), ethanol, and stearic acid (SA), all of which are analytical-grade reagents. MOF HKUST-1 is synthesized through a solvothermal approach utilizing benzene tricarboxylic acid, copper nitrate, and dimethyl formamide. Post-synthetic modification is performed using 150 mM stearic acid in ethanol. The preparation involves precisely weighing 2.4 g of $H_3BTC$ and 4.8 g of $Cu(NO_3)_2:3H_2O$, which are then mixed in 160 mL of DMF using sonication in a polytetrafluoroethylene-lined stainless steel autoclave. The mixture is kept at 80° C. overnight in a preheated oven. After heating, the mixture is cooled and centrifuged at 3500 rpm in a centrifuge device (FC5816) to separate solid crystals from the solvent The separated crystals are washed three times with DMF followed by an ethanol-deionized water (1:2) solution. The washed solids are vacuum-dried overnight at 100° C. in an oven (such as ThermoStable OV-30) to obtain pristine HKUST-1 crystals. Subsequently, 0.5 g of the synthesized HKUST-1 crystals is added to 20 mL of a 150 mM SA solution in ethanol and stirred overnight at room temperature at 300 rpm. Finally, the modified HKUST-1 crystals (SA-HKUST-1) are separated from the SA solution via centrifugation at 3800 rpm, rinsed with ethanol, and vacuum-dried at 100° C. for 20 hours. The schematics of synthesis of SA surface functionalization of HKUST-1 to produce SA-HKUST-1 is provided in Scheme 1.

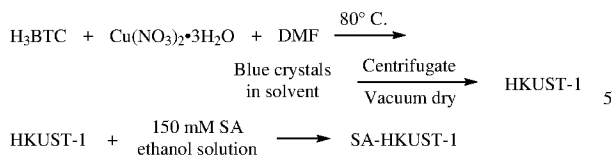

Scheme 1. Synthesis of SA Surface Functionalization of HKUST-1 to Produce SA-HKUST-1

In another embodiment of the present invention, a comprehensive methodology for characterizing the synthesized SA-HKUST-1 is disclosed. The crystalline structure of SA-HKUST-1, both before and after enzyme immobilization, is determined using an X-ray diffractometer (such as PANalytical-XPERT-3). The analysis is conducted with Cu-Kα as the X-ray source at a wavelength of 1.54056 Å within a 2θ range of 10-80°. The generator voltage and current are set at 40 kV and 30 mA, respectively. The functional groups of SA-HKUST-1, with and without enzymes, are identified by Fourier-transform infrared (FT-IR) analysis using an FT-IR instrument (Jasco FTIR-4700 is used for the current experimental setup). Measurements are performed between wavelengths of 4000 and 500 cm$^{-1}$ at a resolution of 4 cm$^{-1}$ with background scans in air across 32 scans. The surface morphology of the hydrophobic MOF, before and after enzyme immobilization, is determined using a scanning electron microscope (for example, JCM-5000, Neoscope). For the analysis, the specimens are coated with gold using a coater (such as JFC-1600 Auto Fine Coater used for current setup) to prevent charge buildup on the surface and to enhance conductivity.

In another embodiment of the invention, the preparation of a multiple enzyme solution containing FDH, GDH and CA and their immobilization on SA-HKUST-1 is disclosed. The multiple enzyme solution is prepared by dissolving 5 mg of CA, 2.5 mg of GDH, and 0.25 mL of FDH solution (containing 1.6 mg of FDH, as determined by the Bradford assay) in 2 mL of deionized (DI) water. The specific activities of CA, GDH and FDH are reported as 3.9 $KU_{CA}$/mg, 23 $U_{GDH}$/mg and 75 $U_{FDH}$/mL respectively. One unit of CA, $U_{CA}$ is defined as the pH drop from 8.3 to 6.3 of $CO_2$ saturated solution in 0.02 M Tris-HCl buffer per minute at 0-4° C., one unit of GDH, $U_{GDH}$, is defined as the amount of GDH consumed to convert 1 μmol $NAD^+$ to NADH in 1 min and one unit of FDH, $U_{FDH}$, is defined as the amount of FDH required to convert one μmole of formic acid to $CO_2$+NADH per minute at pH 7.6 and 25° C. using 41 mM potassium phosphate buffer in the presence of NAD. 1.5 mL of each enzyme solution is mixed together, and 0.5 g of SA-HKUST-1 is added to the resulting multienzyme solution. The mixture is stirred at 25° C. and 120 rpm overnight in a shaking incubator (say SI 300). After the experiment, the MOFs loaded with the enzymes are removed from the enzyme solution by filtration, rinsed three times with deionized water, and dried at −54° C. and 0.02 mbar using a freeze dryer (say LYOQUEST). The immobilized enzymes (E@SA-HKUST-1) are stored between 2° C. and 8° C. in a refrigerator. In an embodiment of the invention, the enzyme loading capacity of SA-HKUST-1 is calculated by quantifying the total proteins before and after adsorption at 25° C. using the standard Bradford assay. In brief, 20 μL of enzyme solution containing the three enzymes is mixed with 180 μL of Bradford reagent and the absorbance is measured at 595 nm using a microplate reader. Protein concentrations are determined by comparing the readings with a standard calibration curve prepared by serial dilution of a standard enzyme solution. The loading capacity of SA-HKUST-1 is calculated using Equation (2):

$$q_e = \frac{(C_i - C_f)}{M} V \tag{2}$$

where $q_e$ (mg/g) is the equilibrium adsorption capacity of SA-HKUST-1, $C_f$ and $C_i$ (mg/mL) are the final and initial protein concentrations in the enzyme solution, V (mL) is the solution volume, and M (g) is the mass of SA-HKUST-1 used. The multienzyme adsorption kinetics on SA-HKUST-1 is analysed by fitting adsorption data at 25° C. to Lagergren pseudo first-order kinetic model as represented by Equation (3) and pseudo second-order kinetic model as represented by Equation (4):

$$\frac{dq_t}{dt} = k_1(q_e - q_t) \tag{3}$$

$$\frac{dq_t}{dt} = k_2(q_e - q_t)^2 \tag{4}$$

where $q_e$ (mg/g) and $q_t$ (mg/g) are enzyme adsorption capacities of SA-HKUST-1 at equilibrium and at any time t, respectively, and $k_1$ (h$^{-1}$) and $k_2$ (mg/g·h) are the pseudo first-order and pseudo second-order rate constants, respectively.

In another embodiment, the diffusion mechanism using Weber-Morris intraparticle diffusion model is analysed as represented by Equation (5):

$$q_t = k_{id} t^{0.5} + C \tag{5}$$

where, $k_{id}$ (mg/g·h$^{0.5}$) is the rate constant for intraparticle diffusion and C is a constant associated with boundary layer thickness around the MOF particle. Large values of C indicate the presence of a thick boundary layer. $q_t$ versus $t^{0.5}$ plot is used to predict the rate constant and rate-limiting step (external film diffusion or intraparticle diffusion through pores of adsorbent) in the adsorption process. The plot shows a straight line if the adsorption is controlled by intraparticle diffusion.

In another embodiment of the present invention, adsorption isotherm analyses are carried out to analyze the enzyme adsorption behavior and mechanism of adsorption on the developed MOF. As further embodiments, the thermodynamics properties of the adsorption process is determined by carrying out the isotherm tests at two temperatures, namely 35° C. and 55° C., which are below the denaturation temperature of the FDH from Candida boidinii used in the experimental setup. The equilibrium adsorption data of multienzyme adsorption on SA-HKUST-1 are fitted to Langmuir isotherm model as represented by Equation (6) and Freundlich isotherm model as represented by Equation (7):

$$q_e = \frac{q_m b C_e}{1 + b C_e} \tag{6}$$

$$q_e = K_F C_e^{\frac{1}{b_F}} \tag{7}$$

where, $q_e$ (mg/g) is the amount of enzyme adsorbed per mass of SA-HKUST-1 at equilibrium, $q_m$ (mg/g) represents the maximum adsorption capacity of SA-HKUST-1, $C_e$ is the concentration of mixed enzymes in solution at equilibrium, b is the solid energy constant related to the heat of adsorption, $K_F$ [(mg/g)·(L/mg)$^{1/bF}$] is the Freundlich constant, and $b_F$ is a dimensionless constant related to the intensity of adsorption and surface heterogeneity. High $b_F$ values suggest high heterogeneity of adsorbent surfaces and strong adsorption.

The constant b in the Langmuir model estimated at various temperatures is useful for predicting thermodynamic parameters, such as change in enthalpy ΔH, Gibbs free energy ΔG, and entropy change ΔS, using Equation (8):

$$\ln(b) = -\frac{\Delta G}{RT} = -\frac{\Delta H}{RT} + \frac{\Delta S}{R} \quad (8)$$

where T (K) is the absolute temperature and R (8.314 J/mol·K) is the universal gas constant.

In an embodiment of the invention, the activity and effectiveness of multi enzymes system is analysed. FDH activity is measured based on NADH consumption during $CO_2$ hydrogenation, using $CO_2$ gas as the substrate, following a modified version of a previously reported procedure. Analytical-grade reagents NaOH, $NaH_2PO_4 \cdot H_2O$, and $Na_2HPO_4 \cdot 7H_2O$ are obtained. Briefly, 5 mL of sodium phosphate buffer at pH 7 is bubbled with $CO_2$ for 1 hour, and the pH of the $CO_2$-saturated buffer is adjusted to 7 using 0.1 M NaOH. Subsequently, 0.5 mL of diluted FDH solution (containing 1.1 mg FDH, as determined by the Bradford assay) and 0.05 g NADH are added to the pH-adjusted buffer, and the reaction is initiated by continuous bubbling of $CO_2$. The reaction is carried out at 25° C. Samples of 300 µL are collected at regular intervals and their absorbance is measured at 340 nm using a microplate reader (such as SPECTROstar Nano). NADH concentrations in the samples are determined based on their absorbance, using a calibration chart prepared with solutions containing known concentrations of NADH.

To analyse the effect of CA on FDH activity, in another embodiment of the invention, the above experiment is repeated under the same operating conditions with the addition of free CA. Specifically, 5 mg of CA is diluted in 2 mL of deionized water, and 0.25 mL of this CA solution is added to the pH-adjusted, $CO_2$-saturated buffer (pH 7) containing 0.5 mL of diluted FDH and 0.05 g of NADH, followed by continuous purging with $CO_2$. NADH concentration is quantified at regular intervals.

In another embodiment of the disclosure, the NADH regeneration efficiency by GDH in the multi-enzyme system is investigated, wherein 5 mL of sodium phosphate buffer (0.1 M) solution of pH 7 is initially purged with $CO_2$ for 1 hour. The pH of the $CO_2$-saturated buffer solution is then adjusted to 7 by adding NaOH. Following this, 3 mL of 10 mM L-glutamic acid is added to the pH-adjusted buffer solution. The required amounts of enzymes (FDH, CA, and GDH), either free or adsorbed on SA-HKUST-1, and 0.05 g of NADH are added to the solution, which is then continuously bubbled with $CO_2$. The reaction is conducted at 25° C. Samples of 0.1 mL are collected at regular intervals, and the formate produced is quantified using a high-performance liquid chromatography (HPLC) apparatus (such as Shimadzu) equipped with a Shodex sugar column (8×300 mm) and a RID detector. A 20 µL sample is injected for analysis, using 5 mM $H_2SO_4$ as the mobile phase at a flow rate of 0.6 mL/min. The HPLC column and detector are maintained at 40° C. Residual NADH concentration in the samples is also determined by measuring their absorbance at 340 nm. All reactions are carried out at 25° C. Control experiments are performed with empty SA-HKUST-1 free of enzymes. The formate yield using free FDH, free multi enzymes and E@SA-HKUST-1 based on initial NADH concentration in the reaction mixtures is calculated using the following Equation (9):

$$\text{Yield} = \frac{c_{HCOOH}}{c_{NADH,initial}} \times 100\% \quad (9)$$

In an embodiment of the present invention, the reusability of the immobilized enzymes is assessed under the same experimental conditions described above. After each reaction cycle, the reaction mixture is centrifuged to recover the enzyme-loaded SA-HKUST-1. The immobilized enzymes are then added to a fresh reaction mixture containing 5 mL of 0.1 M sodium phosphate buffer (pH 7), 3 mL of 10 mM L-glutamic acid, and 0.05 g of NADH. The solution is continuously gassed with $CO_2$, and the formate produced is quantified. The activity recovery of the immobilized enzymes is calculated based on the formate production in the first run, as shown in Equation (10).

$$\text{Activity recovery (\%)} = \frac{\text{Formate produced}}{\text{Formate produced in first run}} \times 100\% \quad (10)$$

The characterization of the synthesized SA-HKUST-1 is performed in various embodiments of the present invention. In one such embodiment, the crystal structure and morphology of HKUST-1, before and after surface modification and enzyme attachment, is analysed. FIG. 1 shows the XRD patterns of HKUST-1, SA-HKUST-1 and E@SA-HKUST-1 and clearly depicts the crystal structure of HKUST-1 before and after surface modification and enzyme attachment. The diffraction peaks at 6.6°, 9.4°, 11.5°, 13.3°, 18.9°, and 25.6° for HKUST-1, SA-HKUST-1, and enzyme-loaded SA-HKUST-1 are consistent with those of simulated HKUST-1 already known. This consistency indicates that the MOF structure is retained after surface modification and enzyme immobilization, attributed to the high hydrophobicity of post-synthetically modified HKUST-1. Modifying HKUST-1 with 150 mM SA increases the static water contact angle from 0° (pristine HKUST-1) to 115°. Scanning electron microscopy (SEM) images (FIG. 1B and FIG. 1 C) show the surface morphology of hydrophobic SA-HKUST-1 before and after enzyme immobilization. After surface modification and enzyme immobilization, the MOF retains its octahedral shape with sharp edges, consistent with the reported morphology of pristine HKUST-1. The surface modification increases the stability of HKUST-1, thereby preventing the disruption of the MOF in the aqueous enzyme solution. This finding is consistent with previous results where FDH immobilization degraded pristine HKUST-1 but not the hydrophobic SA-HKUST-1.

In an embodiment of the invention, the functional groups of enzymes and MOF, before and after enzyme immobilization, are analyzed by FT-IR. FIG. 2A presents the FT-IR spectrum of free enzymes. For free CA, GDH, FDH, and the multienzyme system, the characteristic band at 1640 cm$^{-1}$ corresponds to the C=O stretching and N—H bond of the amide I band in the enzyme secondary structure. FIG. 2B shows the FT-IR spectrum of non-loaded SA-HKUST-1 and enzyme-loaded SA-HKUST-1, that is SA-HKUST-1 before and after enzyme immobilization, respectively. The spectrum of SA-HKUST-1 is consistent with that reported previously, with the band at 728 cm$^{-1}$ corresponding to the stretching vibration of Cu—O. The characteristic bands at 1380 cm$^{-1}$ and 1451 cm$^{-1}$ correspond to the C—O and C=O groups of ionized $H_3BTC$, respectively. The band at 1619 cm$^{-1}$ corresponds to the C=C stretching of the carboxylate group in ionized $H_3BTC$. The bands at 2919 cm$^{-1}$ and 2853 cm$^{-1}$ correspond to the C—H stretching of SA. The appearance of a band at 1640 cm$^{-1}$ for FDH@SA-HKUST-1, CA@SA-HKUST-1, GDH@SA-HKUST-1, and E@SA-HKUST-1 indicates enzyme adsorption on the MOF. The band corresponding to the carboxylate group (1619 cm$^{-1}$) of MOF reduces in intensity and shifts to a lower wave number after enzyme immobilization. In addition, the bands corresponding to C—H stretching reduces in intensity after multienzyme immobilization. This can be due to the formation of hydrogen bonds between the enzymes and MOF.

In another embodiment of the current disclosure, the changes in the secondary structure of enzymes after immobilization on SA-HKUST-1 are assessed using FT-IR by analysing the amide I band between 1600 cm$^{-1}$ and 1700 cm$^{-1}$, which is closely related to protein secondary structure. The amide I bands originate from the C—N bond stretching and in-phase bending of N—H bonds, coupled with the stretching vibrations of C—O bonds. Protein secondary structures (α-helices, β-sheets, β-turns, and random coils) exhibit different amide I band vibrational frequencies due to hydrogen bonds formed with amides. The α-helical content, reflected in the amide I band, influences enzyme folding, and thus their activity, structural rigidity, and stability. Peak deconvolution of the amide I band is performed to resolve the protein spectrum of CA and GDH, which enhance FDH performance. The deconvoluted FT-IR peaks (1600 cm$^{-1}$ to 1700 cm$^{-1}$) of free GDH, CA and FDH and immobilized GDH, CA and FDH (GDH@SA-HKUST-1, CA@SA-HKUST-1 and FDH@SA-HKUST-1) respectively are shown in FIG. 2C-2H, with corresponding secondary structure distributions or assignment presented in FIG. 2I. Immobilization significantly affects the secondary structure of enzymes. For CA and GDH, immobilization increases the α-helical content compared to free enzymes. This increase is more significant for CA, in which the α-helical content increases from 28.8% to 53.0%, while β-sheet content remains at 46%. For GDH, the α-helical content increases from 37.6% to 39.3% upon immobilization. The stability of β-sheet content and the increase in the α-helical content, which are the core secondary structures supporting the active site, generally enhance catalytic activity. Increased activity was reported for CA immobilized on ZIF-L and ZIF-8 previously. However, as previously demonstrated, immobilizing FDH on SA-HKUST-1 drastically reduces its α-helical content from 29.4% to 3.19% and decreases its activity.

In an embodiment of the present invention, an analysis on the adsorption kinetics of the multienzyme system is carried out. The kinetics of the adsorption of multiple enzymes on SA-HKUST-1 at various initial enzyme concentrations are presented in FIG. 3A. An expedited enzyme uptake is observed within the first 2 hours of reaction, followed by a gradual decrease in the rate, and the system reaches equilibrium after approximately 3 hours. The initial high adsorption rate is due to the numerous unoccupied sites available for adsorption, which decrease gradually. Besides, the adsorption capacity increases with the enzyme concentration, due to the higher concentration gradient, which serves as the driving force for adsorption. At high initial enzyme concentrations, the concentration gradient is higher, resulting in a higher rate of enzyme uptake. This agrees well with the results observed for the immobilization of enzymes such as lipase and FDH on HKUST-1 in previous works. Higher adsorption at high enzyme concentrations is also achieved with enzymes such as cellulase and glucuronidase immobilized on other support materials such as UiO66 and clinoptilolite, respectively as reported previously. In an embodiment of the invention disclosed, the kinetics of adsorption of multiple enzymes on SA-HKUST-1 are analysed using pseudo first-order and pseudo second-order kinetic models. Table 1 shows the fitted kinetic parameters of multienzyme adsorption on SA-HKUST-1. It summarizes the model parameters determined by fitting the experimental data at different initial enzyme concentrations. Higher values of $R^2$ indicate that the adsorption of the enzymes on SA-HKUST-1 follows pseudo second-order kinetics. The model curves predicted using the pseudo second-order model are in good agreement with the experimental values, as shown in FIG. 3A.

TABLE 1

Fitted kinetic parameters of multienzyme adsorption on SA-HKUST-1.

| | $q_e$ | Pseudo-first order | | | Pseudo-second order | | |
|---|---|---|---|---|---|---|---|
| $C_o$(mg/mL) | (mg/g) | $q_{cal}$ (mg/g) | $k_1(h^{-1})$ | $R^2$ | $q_{cal}$ (mg/g) | $k_2$(mg/g · h) | $R^2$ |
| 1.66 | — | — | — | — | 103.1 | 0.012 | 0.98 |
| 2.20 | 108.8 | 102.0 | 2.2 | 0.97 | 128.2 | 0.009 | 0.99 |
| 2.34 | 118.3 | 140.7 | 2.9 | 0.96 | 140.8 | 0.008 | 0.99 |
| 2.69 | 134.6 | 163.8 | 2.7 | 0.94 | 158.7 | 0.007 | 0.98 |

Adsorption is influenced by external film diffusion, intraparticle pore diffusion, or a combination of both. The multienzyme absorption mechanism on SA-HKUST-1 is determined using the Weber-Morris model in the present disclosure. FIG. 3B represents the intraparticle diffusion model of multienzyme adsorption on SA-HKUST-1 at different enzyme loadings. A linear plot of $q_t$ against $t^{0.5}$ at different initial enzyme concentrations, as presented in FIG. 3B, displays multilinear plots, suggesting that enzyme adsorption on SA-HKUST-1 is influenced by both intraparticle diffusion and external boundary layer diffusion. The intraparticle diffusion rate constants for these regions in multienzyme adsorption on SA-HKUST-1 are presented in Table 2. The smaller $k_{id}$ values for region 2 (intraparticle diffusion region) than for region 1 (initial steep region/external diffusion region) suggest high intraparticle diffusion resistance for enzyme adsorption on SA-HKUST-1.

TABLE 2

Intraparticle diffusion rate constant of multienzyme adsorption on SA-HKUST-1.

| $C_i$ | Zone 1 | | Zone 2 | |
|---|---|---|---|---|
| (mg/mL) | $k_{id}$(mg/g · h$^{0.5}$) | $R^2$ | $k_{id}$(mg/g · h$^{0.5}$) | $R^2$ |
| 1.67 | 47.3 | 0.98 | 9.5 | 0.89 |
| 2.2 | 55.8 | 0.94 | 8.9 | 0.93 |
| 2.34 | 63.4 | 0.98 | 3.4 | 0.95 |
| 2.69 | 74.3 | 0.99 | 4.4 | 0.79 |

The adsorption isotherms for multienzyme adsorption on SA-HKUST-1 at the two tested temperatures (35° C. and 55° C.) are presented in FIG. 4 (A and B). Increasing the temperature enhances diffusivity toward the support, accelerating the adsorption rate and increasing enzyme adsorption, which is common for protein adsorption. Additionally, at elevated temperatures, the adsorbed enzymes may undergo conformational changes and acquire vibrational energy that in turn promotes the adsorption of new enzyme molecules. The effect of temperature is more pronounced at high enzyme concentrations, as shown in FIG. 4. This is because higher temperatures expose hydrophobic patches on enzymes to the environment, increasing the number of possible hydrophobic interactions between enzymes and the hydrophobic surface. The adsorption isotherms for multienzyme adsorption on SA-HKUST-1 at the tested temperatures are fitted to Langmuir (FIG. 4A) and Freundlich (FIG. 4B) isotherm models. The isotherm model parameters for multienzyme adsorption on SA-HKUST-1 at different temperatures deduced by fitting the experimental data are summarized in Table 3. The data fit well with the Freundlich model, as indicated by the higher $R^2$ values, and the curves predicted by the model, shown in FIG. 4B, are in good agreement with experimental values. The value of $b_F$, related to the intensity of adsorption, is less than 1, indicating the weaker and reversible nature of enzyme adsorption. The increase of $b_F$ with temperature indicates a higher affinity of enzymes for the adsorbent at higher temperatures. The heat of adsorption, $\Delta H$, is estimated using the Langmuir constant b based on Equation (8); the $\Delta H$ value in the present disclosure is found to be 2.55 KJ/mol. The positive value indicates that the adsorption is endothermic and having a value below 40 KJ/mol suggests that it is physisorption. This result suggests that multienzyme adsorption on SA-HKUST-1 mainly occurs through weak hydrogen bonds and hydrophobic interactions.

TABLE 3

Isotherm model parameters for multi enzyme adsorption on SA-HKUST-1 at different temperatures.

| Isotherm | Parameter | 35° C. | 55° C. |
|---|---|---|---|
| Langmuir | $q_m$ | 7070.9 | 9797.773 |
| | b | 0.025 | 0.0271 |
| | $R^2$ | 0.95 | 0.97 |
| Freundlich | $K_F$ | 102.2 | 165.9 |
| | $b_F$ | 0.81 | 0.89 |
| | $R^2$ | 1.00 | 1.00 |

In an embodiment of the present invention, the effectiveness of the multiple enzymes immobilized on SA-HKUST-1 is analysed, using $CO_2$ as substrate at pH 7 in all cases described as follows. The thermodynamic stability of $CO_2$, leading to its poor solubility in water, presents a major challenge in $CO_2$ hydrogenation reactions. The reduction of $CO_2$ to formate by FDH follows the mechanistic steps described in Equations (11) and (12), where the hydration of $CO_2$ to bicarbonate (Equation (10)) is the rate-limiting step:

$$CO_2 + H_2O \leftrightarrow HCO_3^- + H^+ \quad (11)$$

$$HCO_3^- + NADH + H^+ \xleftrightarrow{FDH} HCO_2^- + NAD^+ H_2 \quad (12)$$

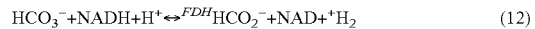

CA catalyzes the conversion of $CO_2$ to carbonate with a high $CO_2$ hydration capacity exceeding 600,000 molecules of $CO_2$ per enzyme molecule. The addition of CA has been reported to increase the reaction rate from $5 \times 10^{-2}$ s$^{-1}$ to $1.6 \times 10^6$ s$^{-1}$. As CA accelerates the conversion of $CO_2$ to carbonate, its presence along with FDH, is therefore expected to enhance the overall reaction rate. To validate this, FDH activity determined is compared by measuring the rate of NADH consumption per mg FDH with and without CA, as shown in FIG. 5A. The addition of CA to the reaction system clearly enhances the activity of FDH, increasing the NADH consumption rate by a factor of 1.4. CA facilitates the dissolution of $CO_2$ to provide $HCO_3$ (Equation (11)) at a faster rate in the reactor, which in turn enhances the uptake of NADH according to Equation (12). By using FDH in a free form, not immobilized, a higher improvement in formate production rate, by a factor of 4.2, is reported with the addition of CA. However, in a bioelectrochemical system, the enhancement in formate production rate with CA addition to free FDH is lower and only 1.18 times higher than that using FDH alone. By using the bioelectrical for $CO_2$ reduction into methanol, the addition of CA resulted in a similar enhancement in FDH activity (1.42 times higher) for formate production.

Another challenge in using FDH for $CO_2$ hydrogenation to formate is the reversibility of the reaction. Higher amount of the produced NAD not only inhibits FDH but also favors the reverse reaction of formate oxidation to $CO_2$ due to FDH's high affinity toward formate. Adding GDH to the system assists in NADH regeneration, thereby maintaining a high NADH concentration and preventing NAD accumulation within the system. To further improve the enzymatic system's effectiveness, GDH is added to FDH and CA, and the efficacy of formate production is assessed. FIG. 5B shows the formate production per mg protein by free FDH, free multi-enzymes and E@SA-HKUST-1. As shown in the figure, after 12 hours of reaction, formate production per mg protein using free FDH alone (10.3 mM/mg protein) is lower than with the multienzyme system in free form (32.3 mM/mg protein), demonstrating the effectiveness of the combined effects of CA and GDH in the multienzyme. The addition of CA enhances the $CO_2$ hydration rate, as shown in FIG. 5A, while GDH ensures a continuous supply of the cofactor NADH. After 6 hours of reaction, the multienzyme system in free form produces three times more formate than free FDH alone under the same reaction conditions. The superior performance exhibited by the multienzyme system is due to faster hydration of $CO_2$ by CA and continuous supply of hydrogen by NADH regeneration by GDH. Similar enhancement of FDH activity was reported when CA and GDH were used in free form for $CO_2$ reduction to formate, followed by conversion of formate to formaldehyde and then to methanol by formaldehyde dehydrogenase and alcohol dehydrogenase respectively. However, methanol yield increased by a factor of 1.31 only with the addition of CA and GDH.

In another embodiment of the present system disclosed, the effectiveness of E@SA-HKUST-1 is assessed based on formate produced per gram of MOF used. FIG. 5C represents the formate production per g MOF using E@SA-HKUST-1. Adding CA and GDH has a more pronounced positive effect with immobilization on hydrophobic SA-functionalized HKUST-1. The developed E@SA-HKUST-1 produces 8.4-fold more formate per gram of MOF than FDH alone attached on SA-HKUST-1. After 3 hours, its production reaches 370.4 mM/$g_{MOF}$, which is over 12- and 1.7-folds higher than that of the same multienzyme system co-encapsulated inside ZIF-8 and polydopamine microcapsules, respectively, under the same operating conditions. Lower production in these other systems is attributed to enzyme encapsulation inside the support matrix, limiting diffusion. The ZIF-8 system almost reached equilibrium within 1 hour and formate production did not exceed 30 mM/$g_{ZIF-8}$, whereas E@SA-HKUST-1 continues to produce formate and attains equilibrium after 6 hours, reaching a production of 1535 mM/$g_{MOF}$. Moreover, using E@SA-HKUST-1, formate production per gram MOF after 6 hours is 9-folds higher than using the same enzyme system co-immobilized on multiple MOFs layers such as that of MIL-101 (Cr) and HKUST-1 in a sequential manner.

In another embodiment of the system presented herein, formate yield based on initial NADH concentration in the reaction mixture shows that after 6 hours, the yield achieved with E@SA-HKUST-1 is 9.74 times higher than with the same enzymes encapsulated in multi-layer MOFs. FIG. 5D shows NADH based formate yield (%) using free FDH, free multi enzymes and E@SA-HKUST-1. In the multilayer MOF system, the innermost MIL-101 (Cr) layer stores adsorbed $CO_2$ and the two HKUST-1 outer layers contains the enzymes. CA is encapsulated in the first HKUST-1 layer, while GDH and FDH are encapsulated in the outer HKUST-1 layer. The lower formate production is due to the slower release of adsorbed $CO_2$ from MIL-101 (Cr) and lower diffusion of $CO_2$ and NADH toward the enzymes, limiting the production. This issue is addressed by the present multienzyme system with surface modification of HKUST-1, for enhancing catalytic performance. SA-HKUST-1's surface hydrophobicity elevates $CO_2$ diffusion toward the MOF surface containing the enzymes and enriches the microenvironment with $CO_2$. Surface hydrophobicity also improves selectivity for formate production. A higher $CO_2$ concentration around CA enhances interaction between the hydrophobic pocket of CA and $CO_2$, thus accelerating $CO_2$ hydration, which is the rate-limiting step in the hydrogenation reaction. Additionally, the interaction between enzymes and SA-HKUST-1's surface leads to conformational changes in the protein structure, favorably affecting their catalytic activity and stability. This positive interaction between the hydrophobic surface of SA-HKUST-1 and enzymes alters the secondary structure of enzymes in a way that enhances the catalytic performance of CA and GDH.

To confirm GDH's effectiveness in regenerating NADH, in an embodiment, the drop in NADH concentration during $CO_2$ hydrogenation process is monitored for the cases of free FDH, free FDH+CA, free multi enzymes (FDH+CA+GDH), empty SA-HKUST-1 and multienzymes immobilized on SA-HKUST-1 (E@SA-HKUST-1). The normalized NADH concentration at time t ($C_t$) with respect to the initial NADH concentration ($C_0$) is presented in FIG. 6. The figure shows drop in normalized NADH concentration at any time t ($C_t$) with respect to the initial NADH concentration ($C_0$) using free FDH, free FDH+CA, free multi enzymes, empty SA-HKUST-1 and E@SA-HKUST-1. Initial concentration of NADH using free FDH, free FDH+CA and empty SA-HKUST-1 is 13.0±0.5 mM, whereas for free multi enzymes and E@SA-HKUST-1, the initial concentration of NADH is 7.5 mM and 8.8 mM, respectively. After 5 hours, NADH concentration dropped to about 70% of the initial value with free FDH. The drop is faster in the presence of CA due to CA's positive effect on the reaction rate, as shown in FIG. 5A. In the presence of GDH, NADH concentration remains almost constant throughout the reaction, demonstrating GDH's regeneration effect. Similarly, stable NADH concentration is observed with enzymes immobilized on SA-HKUST-1, indicating that immobilization did not affect GDH activity. On measuring NADH concentration using empty SA-HKUST-1, it shows an initial slight drop in NADH concentration due to adsorption on SA-HKUST-1, but the concentration remains stable thereafter, confirming that MOF does not interfere with the reaction.

In another embodiment of the given invention, the reusability of E@SA-HKUST-1 is also assessed, which is a crucial factor for industrial applications. Activity recovered after every run of 6-hours is calculated based on formate produced in the first run. FIG. 7A shows the reusability of E@SA-HKUST-1 at pH 7 at 25° C. using $CO_2$ as substrate. The immobilized enzyme system is very stable, retaining 94% of initial enzyme activity after four runs. High stability is attributed to the positive effect of surface modification of the support, enhancing water and acid stability. Increased surface hydrophobicity improves protein adsorption and prevents leaching, as well as increases α-helical content post-immobilization, improving enzyme activity of immobilized enzymes. E@SA-HKUST-1 is more stable than the same multienzyme cascade system on HKUST-1@MIL-101 (Cr), which retains only 57.5% activity after three reuse cycles. This is attributed to the lower stability of outer HKUST-1 layer under the reaction conditions. E@SA-HKUST-1 is also more stable than the multienzyme system encapsulated inside ZIF-8, which retains 65% activity after four cycles of 1-hour each. ZIF-8's lower reusability is due to its poor stability in the presence of acidic $CO_2$ and formate. These results clearly demonstrate the superior performance of multiple enzymes immobilized on the hydrophobic MOF SA-HKUST-1 proposed in the present disclosure.

In another embodiment of the invention, the morphology and crystal structure of immobilized enzymes after repeated use are analyzed to verify the stability of the support. X-ray diffraction and SEM images of E@SA-HKUST-1 after 4 cycles of reuse are obtained for analysis. FIG. 7B and FIG. 7C shows X-ray diffraction (XRD) and scanning electron microscopy (SEM) respectively of E@SA-HKUST-1 after four cycles of use. The samples after repeated use, are almost identical to the freshly prepared samples, confirming the stability of synthesized E@SA-HKUST-1 for use in $CO_2$ hydrogenation. These results demonstrate the potential for developing highly stable biocatalytic systems for continuous transformation of $CO_2$ to formate in a sustainable manner at a commercial level.

In conclusion, the disclosed system herein proposes using a combination of FDH, GDH, and CA enzymes immobilized on a modified hydrophobic MOF, SA-HKUST-1, to enhance $CO_2$ hydrogenation to formate. The hydrophobic support demonstrates a high retention capacity for the enzymes and improves their stability upon repeated use in an aqueous or acidic environments. The addition of CA to the system increases the rate of $CO_2$ hydration, while GDH maintains the concentration of the cofactor NADH necessary for the sustained hydrogenation reaction. This multienzyme system proves to be more efficient than those utilizing the same enzymes immobilized on other MOFs. The proposed novel multienzyme system immobilized on hydrophobic modified HKUST-1 provides an efficient and sustainable solution for the biological conversion of $CO_2$ in industrial applications.

Benefits of the proposed multienzyme system on modified MOF for $CO_2$ hydrogenation in accordance with the present invention include the proposed multi enzymes systems operating at mild conditions using simple equipment and without producing any harmful byproducts. This is an environmentally friendly method. Enzymes are highly specific for reactants and products and can select the desired substrate from a group of molecules. The support (SA-HKUST-1) is highly stable and can be reused. High affinity of the hydrophobic support enhances diffusion of $CO_2$ towards the enzymes compared to the supports used previously.

Many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims, which follow.

The invention claimed is:

1. A biocatalytic multienzyme system for the enhanced hydrogenation of carbon dioxide ($CO_2$) to formate, comprising:
   a hydrophobic modified metal-organic framework (MOF) SA-HKUST-1 as support material, produced by surface-modification of HKUST-1 MOF with stearic acid; and
   a plurality of enzymes comprising formate dehydrogenase (FDH), carbonic anhydrase (CA), and glutamate dehydrogenase (GDH), wherein the plurality of enzymes are immobilized on a hydrophobic surface of the SA-HKUST-1,
   wherein the hydrophobic surface of the SA-HKUST-1 enhances stability and reusability of the plurality of immobilized enzymes.

2. The biocatalytic multienzyme system of claim 1, wherein immobilizing the plurality of enzymes on the hydrophobic surface of the SA-HKUST-1 rather than encapsulating them within its matrix, reduces mass transfer limitations and enhances formate production.

3. The biocatalytic multienzyme system of claim 2, wherein the hydrophobicity of the SA-HKUST-1 improves diffusion of $CO_2$ towards the plurality of immobilized enzymes, enhancing formate production.

4. The biocatalytic multienzyme system of claim 3, wherein the system produces 255.83 mM formate per gram of MOF per hour (mM/gsupport·h).

5. The biocatalytic multienzyme system of claim 1, wherein the FDH converts $CO_2$ to formate using hydrogen donated by nicotinamide adenine dinucleotide+hydrogen (NADH) serving as a cofactor.

6. The biocatalytic multienzyme system of claim 1, wherein the GDH regenerates the cofactor NADH within the system, thereby ensuring a sustained source of hydrogen required for $CO_2$ hydrogenation by the FDH.

7. The biocatalytic multienzyme system of claim 1, wherein the CA accelerates hydration of $CO_2$ and facilitates $CO_2$ capture for hydrogenation by the FDH.

8. The biocatalytic multienzyme system of claim 1, wherein the HKUST-1 MOF undergoes post-synthetic functionalization by treatment with stearic acid in ethanol to produce the hydrophobic modified MOF SA-HKUST-1.

9. The biocatalytic multienzyme system of claim 8, wherein the SA-HKUST-1 is stable and reusable in both acidic and aqueous environments.

10. The biocatalytic multienzyme system of claim 9, wherein the plurality of immobilized enzymes on the SA-HKUST-1 retain at least 95% enzyme activity after four reuse cycles.

11. The biocatalytic multienzyme system of claim 1, wherein the system operates under mild conditions and does not produce harmful byproducts.

12. The biocatalytic multienzyme system of claim 11, wherein the mild conditions comprise a pH of 7 and room temperature.

13. The biocatalytic multienzyme system of claim 1, wherein the formate produced has a high hydrogen storage capacity and is used in hydrogen fuel cells and formic acid-powered vehicles.

14. A method for enhanced hydrogenation of carbon dioxide ($CO_2$) to formate, comprising:
   providing a biocatalytic multienzyme system of claim 1;
   exposing the biocatalytic multienzyme system to $CO_2$ and a hydrogen source; and
   converting $CO_2$ to formate via the catalytic action of the immobilized enzymes.

15. The method of claim 14, wherein the hydrogen source is nicotinamide adenine dinucleotide+hydrogen (NADH) serving as a cofactor.

16. The method of claim 15, wherein the FDH converts $CO_2$ to formate using hydrogen donated by the NADH cofactor, the CA accelerates hydration of $CO_2$, and the GDH regenerates the NADH cofactor within the system.

17. The method of claim 16, wherein the $CO_2$ hydrogenation is carried out under mild conditions comprising a pH of 7 and room temperature and does not produce any harmful byproducts.

18. The method of claim 17, wherein the multienzyme system is reused for multiple cycles while maintaining at least 95% enzyme activity after four reuse cycles.

19. The method of claim 18, wherein the method produces 255.83 mM formate per gram of MOF per hour (mM/gsupport·h).

* * * * *